US006926902B2

United States Patent
Inoue et al.

(10) Patent No.: US 6,926,902 B2
(45) Date of Patent: Aug. 9, 2005

(54) INSECTICIDE TRANSPIRATION APPARATUS

(75) Inventors: Masafumi Inoue, Toyonaka (JP); Koji Nakayama, Toyonaka (JP); Yoshio Katsuda, Nishinomiya (JP)

(73) Assignee: Dainhon Jochugiku Co., Ltd., Osaka (JP)

( * ) Notice: Subject to any disclaimer, the term of this patent is extended or adjusted under 35 U.S.C. 154(b) by 0 days.

(21) Appl. No.: 10/238,626

(22) Filed: Sep. 11, 2002

(65) Prior Publication Data

US 2003/0160062 A1 Aug. 28, 2003

(30) Foreign Application Priority Data

| Feb. 22, 2002 | (JP) | ....................................... 2002-046574 |
| Apr. 12, 2002 | (JP) | ....................................... 2002-110140 |
| Jun. 26, 2002 | (JP) | ....................................... 2002-186138 |

(51) Int. Cl.[7] .......................... A01N 25/10; A01N 53/06
(52) U.S. Cl. .................. 424/409; 43/124; 43/132.1; 424/405; 424/406; 424/408; 424/417; 514/532
(58) Field of Search ................... 424/405, 406, 424/409, 411, 417–421; 514/531, 532; 43/124, 132.1

(56) References Cited

U.S. PATENT DOCUMENTS

| 4,671,435 A | * | 6/1987 | Stout et al. ................. 233/646 |
| 5,230,837 A | | 7/1993 | Babasade |
| 6,179,275 B1 | | 1/2001 | Lagneaux et al. |
| 6,484,438 B2 | * | 11/2002 | Matsunaga et al. ........... 43/129 |
| 2002/0062593 A1 | * | 5/2002 | Matsunaga et al. ........... 43/129 |

FOREIGN PATENT DOCUMENTS

| EP | 0925717 | * | 6/1999 |
| EP | 0 962 139 A1 | | 8/1999 |
| JP | 10 191862 A | | 7/1991 |
| JP | 05 068459 A | | 1/1997 |
| JP | A 2001-247406 | | 9/2001 |

* cited by examiner

Primary Examiner—Neil S. Levy
(74) Attorney, Agent, or Firm—Oliff & Berridge, PLC

(57) ABSTRACT

There is provided an insecticide transpiration apparatus capable of transpiring insecticide at room temperature. The apparatus includes an apparatus main body having a recipient recess capable of accommodating an insecticide cartridge, an insecticide cartridge rotatably supported in the recipient recess, a driving means which is composed of a motor connected to a rotation support shaft of the insecticide cartridge and an electric source and which is contained in the apparatus main body, and a cover pivoted to the apparatus main body so as to cover the insecticide cartridge in the recipient recess, wherein the insecticide cartridge includes an annular hollow structure which accommodates granular insecticide-impregnated bodies and which has openings in an inner peripheral surface and an outer peripheral surface thereof, a core portion situated at the center of the hollow structure and connected to the rotation support shaft, a plurality of spoke portions connecting the core portion and the hollow structure, and blade portions integrally formed with the hollow structure so as to extend from the inner peripheral surface toward the center thereof and adapted to promote passing of air from the inner peripheral surface to the outer peripheral surface of the hollow structure.

20 Claims, 9 Drawing Sheets

INSECTICIDE TRANSPIRATION APPARATUS

BACKGROUND OF THE INVENTION

1. Field of the Invention

The present invention relates to an insecticide transpiration apparatus capable of transpiring insecticide at room temperature, and more specifically, to an insecticide transpiration apparatus in which a chemical cartridge accommodating a chemical impregnated material and having integrally formed blade portions is rotated and in which an airflow resulting from the rotation is utilized to promote the transpiration of the insecticide, making it possible to transpire insecticide continuously from the chemical impregnated material at a fixed transpiration rate and for a long period of time.

2. Description of the Related Art

Known examples of an insecticide transpiration apparatus for transpiring and dispersing insecticide throughout a closed space (e.g., a room of a building or an automobile, or the interior of a tent) in order to exterminate harmful insects, such as mosquitoes and gnats, include apparatuses transpiring insecticide from mosquito-repellent incense, an electric mosquito-repellent mat, a liquid type electric mosquito-repellent unit, etc. by utilizing thermal energy. Generally speaking, insecticide transpiration apparatuses of this type use open fire or electrical energy as a thermal energy source; they are sometimes hard to use from the viewpoint of safety and of securing a power source capable of generating sufficient thermal energy. For example, where use of open fire is dangerous and there is no power source available as in the case of the interior of a tent, it is desirable to use an apparatus capable of transpiring and dispersing a sufficient amount of insecticide at room temperature.

Apparatuses adapted to transpire and disperse insecticide at room temperature without using thermal energy have been proposed; in particular, an apparatus is known which transpires and disperses insecticide at room temperature by utilizing wind force generated by a fan or the like. In an apparatus of this type, in which wind force obtained by a fan or the like is utilized for the transpiration of insecticide, a substantial improvement in insecticide transpiration efficiency is to be expected, as compared to the case in which insecticide (or a chemical impregnated material) is simply allowed to stand for transpiration.

Japanese Patent Application Laid-open No. Hei 10-191862 discloses an apparatus in which granular insecticide-impregnated bodies are accommodated in a still impregnated body accommodating container and in which air from a fan is blown against this to transpire the insecticide while stirring the chemical impregnated material with wind force.

However, the problem with this apparatus is that the chemical impregnated material and the fan are spaced apart too much from each other, so that the wind applied to the chemical impregnated material is rather weak. Thus, in this apparatus, it is difficult for the insecticide to be transpired from the granular substance forming the insecticide-impregnated bodies for a long period of time and at a fixed transpiration rate, and the amount of insecticide transpired decreases with passage of time.

Japanese Patent Application Laid-open No. Hei 5-68459 discloses an apparatus which uses a diffusion material formed by putting, in a sealed manner, a transpirable insecticide in a bag or container having a membrane portion consisting of a gas transmitting film or a bag or container having minute pores with breathability; by rotating this diffusion material, the transpirable insecticide is diffused into the air.

In the diffusion material used in this method, however, it is rather difficult to efficiently transpire the insecticide from the entire transpirable insecticide; thus, a decrease in the amount of insecticide transpired with passage of time is inevitable.

SUMMARY OF THE INVENTION

The present invention has been made with a view toward solving the above-mentioned problems in the conventional insecticide transpiration apparatuses. It is an object of the present invention to provide an insecticide transpiration apparatus which is capable of transpiring insecticide for a long period of time, e.g., ten days or more, without using thermal energy and which, as a result, provides many advantages; for example, it prevents a decrease in transpiration amount with passage of time, is applicable outdoors, sustains a superior insecticidal effect, and provides a high level of safety and satisfactory usability.

After careful study to achieve the above object, the present inventors have found the following fact to thereby complete the present invention: by accommodating a chemical impregnated material in an annular hollow structure with integrally formed blade portions and rotating the hollow structure to create an airflow from the inner peripheral surface toward the outer peripheral surface thereof to thereby promote the transpiration of the insecticide, it is possible to maintain a stable transpiration performance for a long period of time (e.g., for 30 days when used 12 hours per day).

That is, the present invention relates to an insecticide transpiration apparatus including:
  an apparatus main body having a recipient recess capable of accommodating an insecticide cartridge;
  an insecticide cartridge rotatably supported in the recipient recess;
  a driving means which is composed of a motor connected to a rotation support shaft of the insecticide cartridge and an electric source and which is contained in the apparatus main body; and
  a cover pivoted to the apparatus main body so as to cover the insecticide cartridge in the recipient recess,
  wherein the insecticide cartridge includes:
    an annular hollow structure which accommodates granular insecticide-impregnated bodies and which has openings in an inner peripheral surface and an outer peripheral surface thereof;
    a core portion situated at the center of the hollow structure and connected to the rotation support shaft;
    a plurality of spoke portions connecting the core portion and the hollow structure; and
    blade portions integrally formed with the hollow structure so as to extend from the inner peripheral surface toward the center thereof and adapted to promote passing of air from the inner peripheral surface to the outer peripheral surface of the hollow structure.

The present invention may assume the following preferred forms:
  (a) an insecticide transpiration apparatus, wherein the hollow structure is composed of a main body member and a cover member engaged therewith;

(b) an insecticide transpiration apparatus, wherein the openings consist of a multitude of opening slits formed in parallel;
(c) an insecticide transpiration apparatus, wherein the blade portions consist of arcuate or curved blades having a length of at least 5 mm or more;
(d) an insecticide transpiration apparatus, wherein the insecticide-impregnated bodies have an average outer diameter of 3 to 10 mm and a size not less than 1.3 times that of the openings;
(e) an insecticide transpiration apparatus, wherein the insecticide-impregnated bodies are accommodated in the insecticide cartridge at a void ratio of 20 to 70%;
(f) an insecticide transpiration apparatus, wherein the chemical impregnated material includes a fluorine-substituted benzyl alcohol ester compound represented by formula (I):

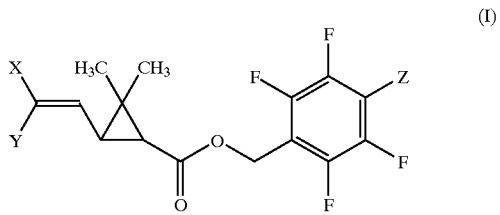

wherein X and Y are identically or differently represent hydrogen atom, methyl group, halogen atom or trifluoromethyl group, and Z represents hydrogen atom, fluorine atom, methyl group, methoxymethyl group or propargyl group, or a mixture thereof;
(g) an insecticide transpiration apparatus, wherein the chemical impregnated material includes a chemical selected from 2,3,5,6-tetrafluorobenzyl-chrysanthemate, 2,3,5,6-tetrafluorobenzyl-2,2-dimethyl-3-(2,2-dichlorovinyl)cyclopropane carboxylate, 4-methyl-2,3,5,6-tetrafluorobenzyl-chrysanthemate, 4-methyl-2,3,5,6-tetrafluorobenzyl-2,2-dimethyl-3-(1-propenyl) cyclopropane carboxylate, 4-methyl-2,3,5,6-tetrafluorobenzyl-2,2-dimethyl-3-(2,2-difluorovinyl) cyclopropane carboxylate, 4-methoxymethyl-2,3,5,6-tetrafluorobenzyl-chrysanthemate, 4-methoxymethyl-2,3,5,6-tetrafluorobenzyl-2,2-dimethyl-3-(1-propenyl) cyclopropane carboxylate, 2,3,4,5,6-pentafluorobenzyl-2,2-dimethyl-3-(2-chloro-2-trifluoromethylvinyl) cyclopropane carboxylate, 4-propargyl-2,3,5,6-tetrafluorobenzyl-3-(1-propenyl)-2,2-dimethylcyclopropane carboxylate, 4-methoxymethyl-2,3,5,6-tetrafluorobenzyl-2,2,3,3-tetramethylcyclopropane carboxylate and 4-propargyl-2,3,5,6-tetrafluorobenzyl-2,2,3,3-tetramethylcyclopropane carboxylate, or mixtures thereof;
(h) an insecticide transpiration apparatus, wherein the chemical impregnated material includes 60 mg or more of the chemical;
(i) an insecticide transpiration apparatus, wherein the chemical impregnated material includes a substrate made of paper, pulp, cellulose-based carrier or synthetic resin carrier, or a mixture thereof;
(j) an insecticide transpiration apparatus, wherein the rotational frequency of the motor is in the range of 500 to 2000 rpm;
(k) an insecticide transpiration apparatus, wherein the chemical can be transpired from the chemical impregnated material at a transpiring amount of 0.01 to 0.6 mg per hour for 180 hours or more;
(l) an insecticide transpiration apparatus, wherein the insecticide cartridge is made of a polyester resin;
(m) an insecticide transpiration apparatus, wherein the polyester resin is polyethylene terephthalate;
(n) an insecticide transpiration apparatus, wherein the polyethylene terephthalate has an intrinsic viscosity of 0.7 dl/g or less;
(o) an insecticide transpiration apparatus, further including an insecticide remaining amount display function realized by liquid crystal and allowing visual inspection;
(p) an insecticide transpiration apparatus, wherein the insecticide remaining amount display function is in correspondence with a plurality of insecticide cartridges of different valid periods of use, wherein a magnetic sensor or an optical sensor adapted to detect a signal from a magnetic tape or a metal member attached to the cartridge is provided on the surface of the insecticide transpiration apparatus opposed to the cartridge, and wherein a central processing unit receives the signal detected by the sensor to recognize the kind of cartridge;
(q) an insecticide transpiration apparatus which contains a circuit adapted to emit pulses of a natural frequency with the operation of the motor, wherein the central processing unit detects these pulses emitted to measure the motor operation time on the basis thereof and controls the display of the insecticide remaining amount;
(r) an insecticide transpiration apparatus, further including a battery remaining power indicating function realized by liquid crystal and allowing visual inspection; and
(s) an insecticide transpiration apparatus, wherein the battery remaining power indicating function is realized by a display portion, a voltage reduction detecting circuit, and a central processing unit adapted to recognize a reduction in battery voltage and control the battery remaining power indication on the basis of the recognition.

The insecticide transpiration apparatus of the present invention is characterized in that it uses an insecticide cartridge consisting of an annular hollow structure with integrally formed blade portions. Comparison of the insecticide cartridge of the present invention, in which the blade portions are formed integrally with the hollow structure, with the insecticide cartridge of the comparative example, in which the hollow structure accommodating insecticide and the blade portions are formed as separate members, shows that in the insecticide cartridge of the comparative example, it is necessary to provide an annular support portion (of a structure similar to that of the inner peripheral surface portion of the hollow structure) for supporting each blade portion, whereas, in the insecticide cartridge of the present invention, no such annular support portion is needed. Thus, in the insecticide cartridge of the present invention, it is possible to further increase the length of the blade portions, so that it is possible to generate a stronger air flow; further, the airflow generated by the blade portions can blow against the insecticide-impregnated bodies without weakening. For these reasons, it is useful in improving the transpiration efficiency to form the blade portions for generating airflow integrally with the hollow structure. Further, the integration of the blade portions and the hollow structure is advantageous also from the viewpoint of productivity since it makes it unnecessary to separately produce the blade portions and the hollow structure and then assemble them. In particular, when the blade portions are separately produced and mounted to the hollow structure, it is necessary to exercise care to prevent the blade portions from blocking the openings provided in the inner peripheral surface of the hollow structure, so that the assembly is a bother. In contrast, in the case in which the hollow structure and the blade portions are formed integrally, the blade portions are provided where there are no openings at the design stage, whereby it is possible to prevent the openings of the inner peripheral surface of the hollow structure from being blocked by providing the blade portions where there are no openings, which also contributes to a substantial improvement in productivity.

DETAILED DESCRIPTION OF THE INVENTION

In the insecticide transpiration apparatus of the present invention, the insecticide cartridge containing insecticide-impregnated bodies is rotated by a rotating means, whereby the insecticide is transpired at room temperature, with a centrifugal force acting on the insecticide-impregnated bodies. In this case, the centrifugal force acting on the insecticide-impregnated bodies provides the following various effects, thus contributing to a stable transpiration of insecticide for a long period of time.

1) The insecticide-impregnated bodies are previously contained in the insecticide cartridge in a desirable state. However, since each chemical impregnated material is not secured in position, the insecticide-impregnated bodies move when an impact is applied to the insecticide cartridge or when the insecticide cartridge is moved, resulting in a change in the state in which the insecticide-impregnated bodies are contained in the insecticide cartridge. However, when in use a centrifugal force acts on the insecticide-impregnated bodies, the insecticide-impregnated bodies are pressurized toward the outer peripheral surface of the insecticide cartridge, whereby the preferable containing state is restored.

2) When the action of the centrifugal force on the insecticide cartridge is cancelled, each chemical impregnated material moves freely to some degree as a result of the rotation or movement of the insecticide cartridge, and changes its position Thus, by causing the centrifugal force to act on the insecticide cartridge or canceling the action, each chemical impregnated material is moved, thus providing an effect as if the insecticide-impregnated bodies are stirred.

3) When a centrifugal force is applied to the insecticide-impregnated bodies, the insecticide in the insecticide-impregnated bodies is pushed toward the surface by the centrifugal force, and the evaporation thereof is promoted by the airflow created by the rotation of the insecticide cartridge, making it possible to effectively evaporate the insecticide in the insecticide-impregnated bodies.

The magnitude of the centrifugal force is determined according to the rotating condition of the insecticide cartridge. For example, the magnitude of the centrifugal force may be 1/1000 to 100 times the gravitational acceleration ($9.8 \times 10^2$ cm/s$^2$); specifically, it may be $9.8 \times 10^{-1}$ cm/s$^2$ to $9.8 \times 10^4$ cm/s$^2$.

The insecticide cartridge in the insecticide transpiration apparatus of the present invention consists of an annular hollow structure having a hollow portion for containing the insecticide-impregnated bodies. The size of the hollow structure varies according to the amount of insecticide-impregnated bodies to be contained so as to achieve a desired transpiration amount. The insecticide cartridge may assume an arbitrary configuration; for example, the hollow structure may have a rectangular sectional configuration.

It is desirable for the hollow structure to be formed by a main body member having an annular groove and a cover member serving as a cover for the groove from the viewpoint of the preparation of the hollow structure, the accommodation of the insecticide-impregnated bodies in the hollow structure, etc.

The annular hollow structure constituting the insecticide cartridge of the present invention has openings in its outer peripheral surface and inner peripheral surface, the openings serving as the breather for transpiring insecticide. There is no particular limitation regarding the design of the openings as long as they provide sufficient permeability; it is desirable that the ratio of the total area of the openings to the total area of the insecticide cartridge peripheral surface be set, for example, to 1:10 to 1:2.

The configuration of the openings may be such that a net is fixed to the opening slits or the holder. Preferably, a large number of opening slits are formed in parallel.

Further, in order to prevent insecticide from being transpired before use from the insecticide-impregnated bodies accommodated in the insecticide cartridge, it is desirable to attach an intercepting member, such as a sealing tape, to the openings of the insecticide cartridge. Since it must be removed at the time of use, the intercepting member is preferably in the form of an adhesive tape or the like that can be easily peeled off.

In the insecticide cartridge of the present invention, blade portions extending toward the center of the hollow structure are integrally formed at positions where they do not block the openings in the inner peripheral surface of the hollow structure. The blade portions have a configuration such that they promote passing of air from the inner peripheral surface toward the outer peripheral surface of the hollow structure through rotation of the insecticide cartridge.

There is no particular limitation regarding the length of the blade portions; it is preferably not less than 5 mm. The strength of the airflow generated through the rotation of the insecticide cartridge can be adjusted by varying their configuration. For example, the longer the blade portions, the stronger the airflow generated. Further, when the blade portions are of an arcuate or curved configuration, it is possible for the blade portions to send more air toward the outer peripheral surface of the hollow structure.

At the center of the annular hollow structure constituting the insecticide cartridge, there exist a rotation support shaft connected to a drive means for rotating the insecticide cartridge and a core portion joined to the rotation support shaft. The core portion may be of any construction as long as the insecticide cartridge and the rotation support shaft can be connected without play. For example, it is possible to use a cylindrical member to be fitted onto the rotation support shaft without play.

The core portion is connected to the hollow structure by a plurality of spoke portions. It is possible to use an arbitrary number of spoke portions. For example, it is desirable to connect the hollow structure and the core portion by two through four spoke portions, in particular, three or four spoke portions.

In the present invention, the insecticide cartridge may be preferably made of a polyester resin in point of workability and usability. The polyester resin may be polyethylene terephthalate, polybutylene terephthalate, polyacrylate, polycarbonate or the like. Among them, polyethylene terephthalate is particularly preferable.

In the present invention, furthermore, it is preferable that the above intrinsic viscosity of polyethylene terephthalate may be 0.7 dl/g or less when it is measured at 25° C. in a mixture solvent of phenol/1,1,2,2-tetrachloroethane (weight ratio=1/1). When the intrinsic viscosity of polyethylene terephthalate is in such a range, the insecticide cartridge of the present invention is excellent in its strength and moldability and is capable of efficiently releasing the chemical components without loss when the insecticide cartridge is in use. Furthermore, the above resin may be added with a lubricant (e.g., paraffin wax, fatty acid ester or aliphatic alcohol), a stabilizer (e.g., calcium or zinc containing compound), an impact strength reinforcing agent, an antioxidant, an ultraviolet absorber, a weatherproof modifier, a pigment, a processing aid, a heat-resistant modifier or the like, to the extent that does not affect the characteristics of the present invention.

The chemical impregnated material to be used in the insecticide transpiration apparatus can be deformed into various forms. It may be a granulated material of, such as spherical, elliptical, oval, columnar, prismatic, cylindrical, discoidal, rectangular or indefinite shape.

More preferably, a chemical impregnated material in a particulate form having an average outer diameter of 3 mm to 10 mm which is 1.3 times larger than the diameter of the opening. Adopting such the chemical impregnated material having such size and shape allows to keep a stable transpiring amount for a long time because of the gradual migration of chemical components included in the chemical impregnated material to the surface thereof. On the other hand, for example, if the chemical impregnated material is less than 3 mm in average diameter, the chemical can be transpired too fast, resulting in problems with respect to the persistence of insecticidal efficiency.

The chemical impregnated material is housed in the insecticide cartridge with a free volume (i.e., the ratio (%) of an inner volume remained as a space unfilled with the chemical impregnated material) of 20% to 70%, preferably 25% to 65%, more preferably 30% to 60%. If the free volume of the insecticide cartridge is less than 20%, the flow of air becomes difficult to pass through the insecticide cartridge and a sufficient transpiring amount of the chemical cannot be obtained. On the contrary, if the free volume of the insecticide cartridge is higher than 70%, the duration of contact between the air and the chemical impregnated material when the air passes through the insecticide cartridge becomes shortened, so that a sufficient transpiring amount of the chemical cannot be obtained.

Preferably, the chemical impregnated material may include a chemical having a transpiring amount, which can be adjusted to 0.01 to 0.6 mg per hour and sufficient insecticide effects by such a chemical amount. In particular, such a chemical may include a transpirational pyrethroid-base insecticide. For instance, the transpirational pyrethroid insecticide may be a fluorine-substituted benzyl alcohol ester compound represented by formula (I):

(I)

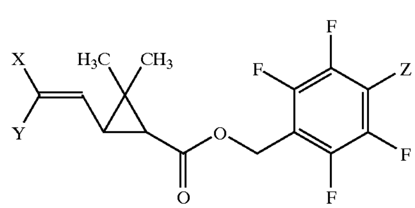

wherein X and Y are identically or differently represent hydrogen atom, methyl group, halogen atom or trifluoromethyl group, and Z represents hydrogen atom, fluorine atom, methyl group, methoxymethyl group or propargyl group.

As a specific example of a compound expressed by formula (I), one selected from the following chemicals may be given: 2,3,5,6-tetrafluorobenzyl-chrysanthemate; 2,3,5,6-tetrafluorobenzyl-2,2-dimethyl-3-(1-propenyl)cyclopropane carboxylate; 4-methyl-2,3,5,6-tetrafluorobenzyl-chrysanthemate; 4-methyl-2,3,5,6-tetrafluorobenzyl-2,2-dimethyl-3-(2,2-dichlorovinyl)cyclopropane carboxylate; 4-methyl-2,3,5,6-tetrafluorobenzyl-2,2-dimethyl-3-(2,2-difluorovinyl)cyclopropane carboxylate; 4-methoxymethyl-2,3,5,6-tetrafluorobenzyl-chrysanthemate; 4-methoxymethyl-2,3,5,6-tetrafluorobenzyl-2,2-dimethyl-3-(1-propenyl)cyclopropane carboxylate; 2,3,4,5,6-pentafluorobenzyl-2,2-dimethyl-3-(2-chloro-2-trifluoromethylvinyl)cyclopropane carboxylate; and 4-propargyl-2,3,5,6-tetrafluorobenzyl-3-(1-propenyl)-2,2-dimethylcyclopropane carboxylate. Further, as examples of compounds other than those expressed by formula (I), the following chemicals may be given: 4-methoxymethyl-2,3,5,6-tetrafluorobenzyl-2,2,3,3-tetramethylcyclopropane carboxylate; and 4-propargyl-2,3,5,6-tetrafluorobenzyl-2,2,3,3-tetramethylcyclopropane carboxylate.

Furthermore, there are optical and geometrical isomers as the above compound includes asymmetric carbon atoms and double bonds. As a matter of course, such isomers and any mixtures thereof can be used as the above chemicals.

Moreover, the chemical impregnated material may contain one kind of a chemical or alternatively may contain a mixture of two or more kinds of chemicals.

On the other hand, it is not preferable to use allethrin, prallethrin, and so on, which have been conventionally used as active constituents of heat-transpiration insecticides, in the present insecticide transpiration apparatus because of their poor transpiration abilities at ambient temperatures. In addition, even if it is a pyrethroid-based insecticide, chemicals such as empenthrin which exhibits a high vapor pressure is also not preferable because it requires a transpiring amount of 2 mg or more per hour for exerting its effective insecticidal effects.

Preferably, the chemical impregnated material may include 60 mg or more of the chemical. If the amount of the chemical is less than 60 mg, there is a fear of which the insecticidal effects cannot be sustained sufficiently. At the time of impregnating the chemical, if required, a solvent, a diluent, a surfactant, a dispersant, a sustained release preparation, or the like can be used and also any conventional means for impregnating can be applied. The chemical impregnated material may include a stabilizer, an aroma chemical, a colorant, an antistatic agent, or the like, as far as the transpiration of the chemical is not interfered. In addition, it is also possible to prepare a multi-purpose chemical composition by the addition of other insecticides/repellent components which have a high transpirational property such as an insect proofing aroma chemical (e.g., hinokitiol, carvone, safrole, citronellol, or cinnamaldehyde), miticide, bactericide or deodorant.

As chemical impregnated materials, for example, materials include paper, pulp, cellulose-based carriers such as viscose, synthetic resin carriers such as ethylene-vinyl acetate-based resin and olefin polymer, and inorganic carriers such as calcium silicate. Among them, preferable is one having a substrate prepared from paper originated from a natural raw material, pulp, a cellulose-based carrier or a synthetic resin carrier, or a mixture thereof.

In the insecticide transpiration apparatus of the present invention, various kinds of chemical impregnated materials with different dimensions, shapes, chemicals to be included, materials, and so on, may be mixed together at a preferable ratio and may be then housed in a insecticide cartridge. Simultaneously using the chemical impregnated materials with different transpiring properties, availabilities and so on, the insecticide transpiration apparatus of the present invention may attain combined insecticidal and insect repellent effects.

The drive means for rotating the insecticide cartridge in the insecticide transpiration apparatus of the present invention consists of a motor and an electric source, which are contained in the apparatus main body. From the viewpoint of making the service life of the insecticide transpiration apparatus as long as possible, it is desirable for the motor to be of a power saving type. For example, a drive means capable of maintaining 500 to 2000 rpm for not less than 300 hours with at least one battery of 2.0–3.0V voltage is preferable. The electric source may be a battery, such as dry cell with 3.0–6.0V, or a direct current electric source with 3.0–6.0V produced by the voltage drop of an alternating current through an AC adapter. Even when an alternating current is used as an electric source in order to secure stable transpiration and low use cost, it is preferable to set so as to use a battery, for example, for using outdoors, in addition to the alternating current.

In the insecticide transpiration apparatus of the present invention, the insecticide cartridge rotates during use, so that if the insecticide cartridge is exposed, a problem is involved from the viewpoint of safety, etc. Thus, in the insecticide transpiration apparatus of the present invention, the insecticide cartridge is accommodated in the recipient recess of the apparatus main body, and is further covered with a cover. However, in order that the cover may not hinder the transpiration of the insecticide, it is desirable to provide an opening in the cover. Thus, in the periphery of the cover, there are provided openings in the form of slits, meshes or the like; further it is desirable for the cover to be constructed such that it does not allow a finger or the like to touch the rotating insecticide cartridge. When the insecticide has been used up, it is necessary to replace the insecticide cartridge; in view of this, the cover is pivotally mounted to the apparatus main body.

In the insecticide transpiration apparatus of the present invention, it is possible to arbitrarily change the amount of insecticide transpired from the insecticide-impregnated bodies and the insecticide transpiration duration period by varying various factors related to the above-mentioned constructions, e.g., the size of the insecticide cartridge, the total area of the openings provided in the insecticide cartridge, the size and configuration of the blade portions, the amount and filling factor of the insecticide-impregnated bodies accommodated in the insecticide cartridge, the kind and amount of insecticide contained in the insecticide-impregnated bodies, the size and configuration of the insecticide-impregnated bodies, and the rotating speed of the insecticide cartridge. For practical use, it is particularly desirable to construct the insecticide transpiration apparatus such that insecticide can be transpired from the insecticide-impregnated bodies for not less than 180 hours in an amount of 0.01 to 0.6 mg per hour.

The insecticide transpiration apparatus of the present invention may be further equipped with an insecticide remaining amount indicating function realized by liquid crystal to allow visual inspection and/or a battery remaining power indicating function. Such indicating functions are controlled by a built-in central processing unit (CPU), a memory or the like; for example, when indicating insecticide remaining amount for a plurality of types (usually two or three types) of cartridges of different valid use periods, it is desirable to adopt a system in which a magnetic sensor or an optical sensor is provided on the surface of the apparatus opposed to the cartridge and in which a CPU receives a signal detected by the sensor to recognize the type of cartridge. However, the insecticide remaining amount indicating function may be changed by manually operating according to two or three cartridges having different valid use periods. The different cartridge types may, for example, be classified by valid use period as follows: 240 hours type (20 days when used twelve hours a day), 360 hours type (30 days when used twelve hours a day), and 720 hours type (60 days when used twelve hours a day).

Further, various control systems are possible for the insecticide remaining amount indicating function. For example, it is possible to adopt a system in which a built-in RC oscillation circuit emits pulses of a specific frequency when the motor operates under a voltage not less than a predetermined magnitude and in which the oscillation pulses are detected and the motor operation time is measured based thereon, conversion to insecticide remaining amount being controlled. Usually, a memory is provided, and the timer data is stored so as not to be erased if the power source is turned off. Further, it is desirable to adopt an arrangement in which the motor operation time measurement program is reset by depressing a reset switch after replacement of the cartridge.

The configuration and display design of the insecticide remaining amount display portion may be arbitrarily selected. For example, it is possible to provide bar-like liquid crystal display portions in a number corresponding to the cartridge types; it is also possible to realize a switching display with a single liquid crystal display portion.

The battery remaining power indicating function can be realized by a display portion, a voltage reduction judgment circuit, and a CPU recognizing the battery voltage and controlling the indicating function based on the recognition. The configuration and display design of the battery remaining power display portion may be arbitrarily selected. Further, it may be integrated with the insecticide remaining amount display portion or provided as a separate component.

Any suitable means for indicating the insecticide remaining amount or the battery remaining power may be applied. For example, the means may be bar-like indicator the length of which brightened indicates the amount or power, or some rectangular indicators the number of which brightened indicates the amount or power. In addition, the indicator may be set so that it may blink at the end point thereof in order to make clear the time for replacing the cartridge or battery.

BRIEF DESCRIPTION OF THE DRAWINGS

In the accompanying drawings!

DESCRIPTION OF THE PREFERRED EMBODIMENTS

Figure 1:
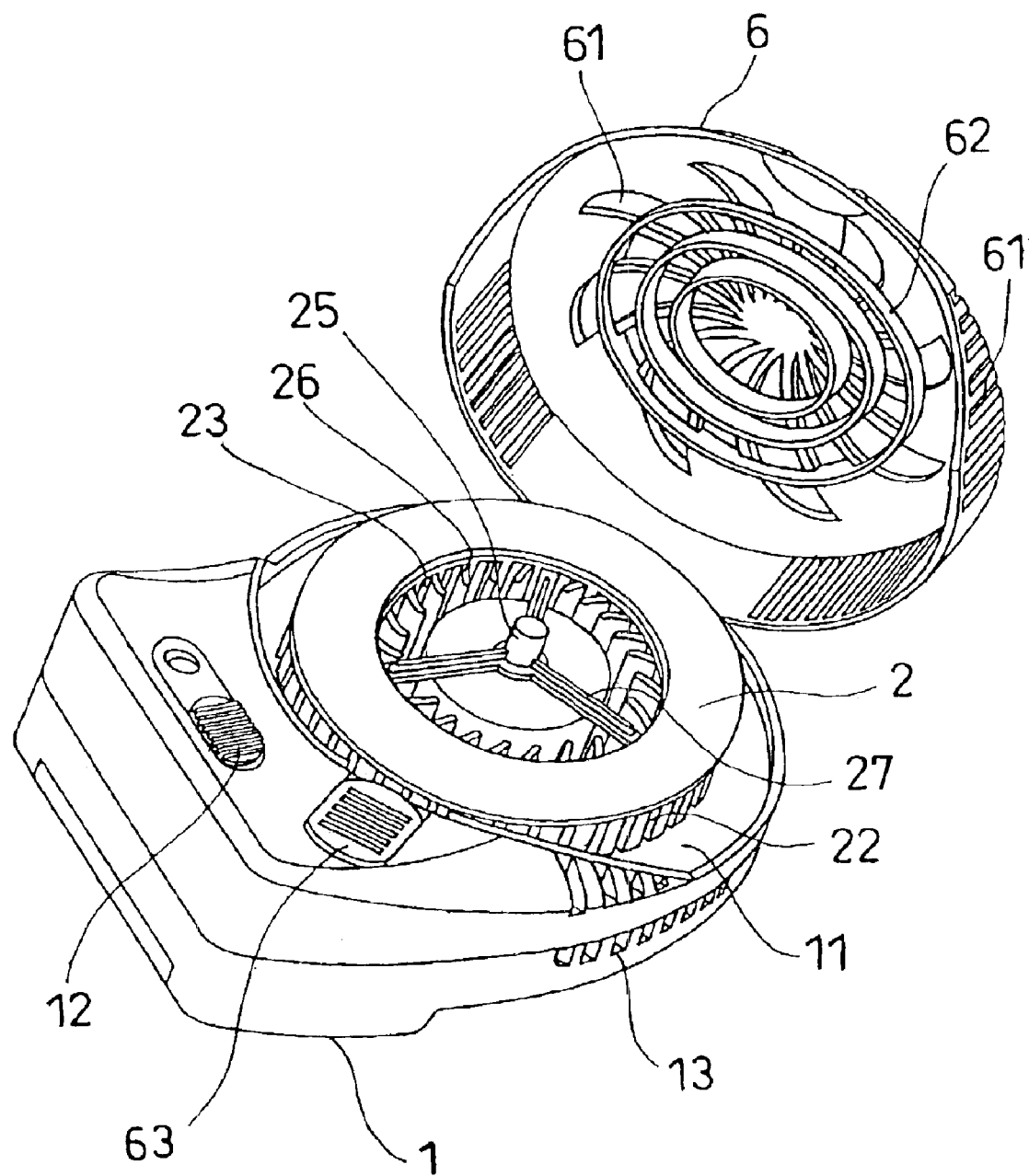
FIG. 1 is a perspective view of an insecticide transpiration apparatus according to the present invention.
Figure 2:
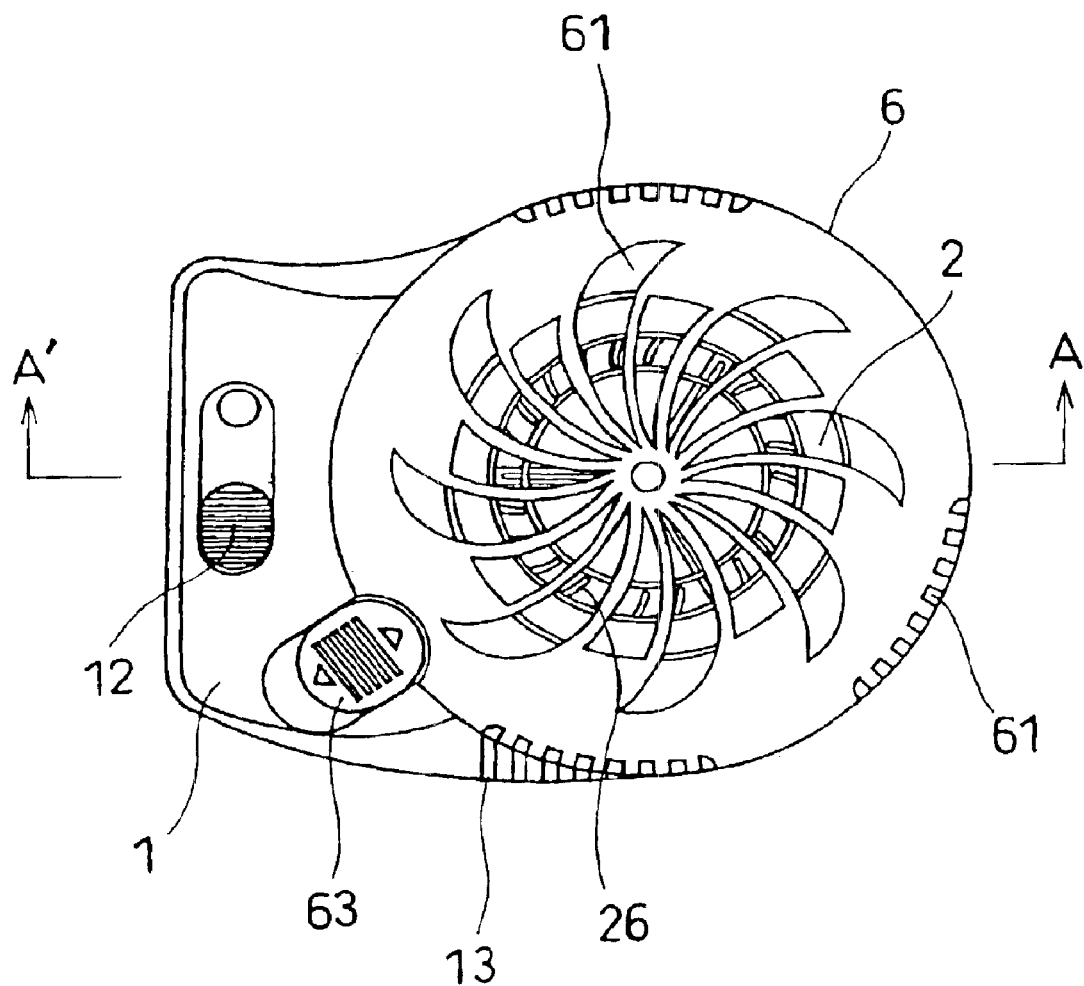
FIG. 2 is a front view of an insecticide transpiration apparatus according to the present invention.
Figure 3:
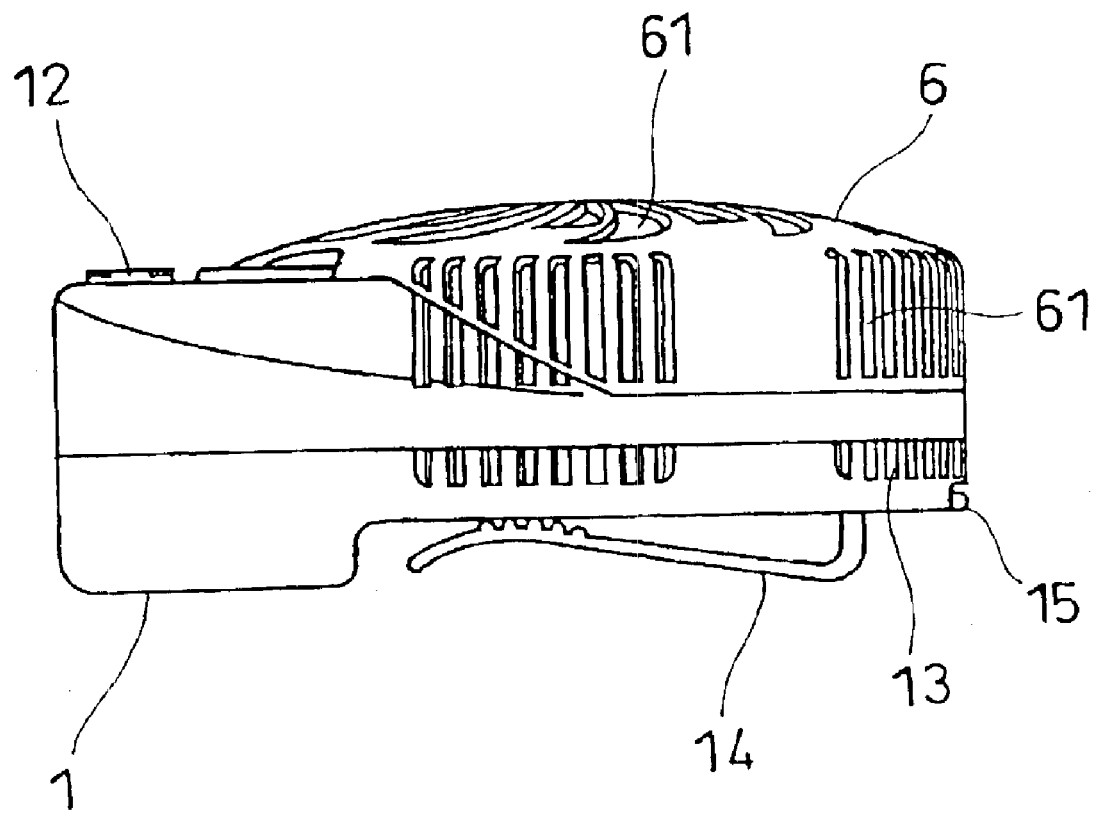
FIG. 3 is a side view of an insecticide transpiration apparatus according to the present invention.

The apparatus of the present invention will now be described in more detail with reference to the drawings.

As shown in FIGS. 1 through 4, an insecticide cartridge 2, which is accommodated in a recipient recess 11 of an apparatus main body 1 and rotatably supported therein, contains insecticide-impregnated bodies 3, and is rotated by a motor 4 driven by batteries 5. The insecticide cartridge 2 is covered with a cover 6 so that it may not be exposed.

The apparatus main body 1 is a member which accommodates the insecticide cartridge 2 in its recipient recess 11 and which contains the drive means consisting of the motor 4 and the batteries 5. Further, the apparatus main body has on its surface a power switch 12 for controlling the driving/stopping of the insecticide cartridge 2. Further, it is preferably provided with openings 13 so as not to hinder the transpiration of the insecticide.

Further, a holder 14 is provided on the back surface (the surface opposite to the side where the insecticide cartridge is provided) so that the apparatus can be attached to the clothes, or a string is passed through a suspending portion 15 provided in the upper portion of the apparatus main body 1 so that the apparatus can be suspended from the neck, whereby the insecticide transpiration apparatus can be carried about very easily. Further, from the viewpoint of portability, it is desirable that the size of the apparatus main body 1 be as small as possible.

Figure 4:
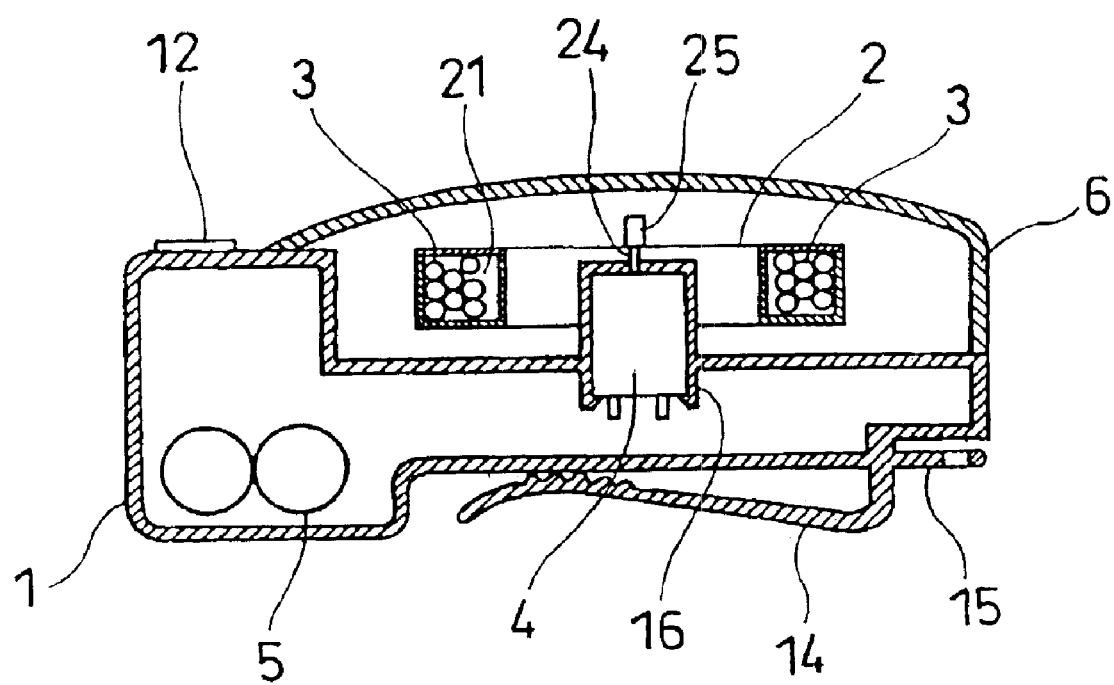
FIG. 4 is a schematic sectional view taken along the line A-A' of FIG. 2.

As shown in FIG. 4, the insecticide-impregnated bodies 3 are contained in a hollow structure 21 of the insecticide cartridge 2. It is not always necessary to fill the hollow structure 21 fully with the insecticide-impregnated bodies 3, for, due to the centrifugal force generated through the rotation of the insecticide cartridge 2, the insecticide-impregnated bodies 3 are pressed against the outer peripheral surface of the insecticide cartridge 2, and the insecticide-impregnated bodies 3 exist densely near the outer peripheral surface of the insecticide cartridge 2.

From the viewpoint of preventing their scattering, the size of the insecticide-impregnated bodies 3 must be at least larger than the size of the openings 22 of the outer peripheral surface and that of the openings 23 of the inner peripheral surface.

The motor 4 is situated under the insecticide cartridge 2, and is mounted to the apparatus main body 1 by means of a motor mounting portion 16. The motor 4 is connected to a rotation support shaft 24 of the insecticide cartridge 2, and the rotation support shaft 24 is connected to a core portion 25 of the insecticide cartridge 2. The connection between the motor 4 and the rotation support shaft 24 and between the rotation support shaft 24 and the core portion 25 must be firm enough not to involve slippage when driving the motor 4; however, when the insecticide in the insecticide-impregnated bodies 3 has been used up and the insecticide cartridge 2 is to be replaced, it is desirable for the insecticide cartridge 2 and the motor 4 to be capable of being easily separated from each other.

The motor 4 is driven by the batteries 5 contained in the apparatus main body 1. It is desirable to provide an opening for battery replacement in the apparatus main body 1 to allow the batteries 5 to be replaced when they have been used up.

In the insecticide transpiration apparatus of the present invention, the insecticide cartridge 2 rotates at high speed during use, so that in order to prevent a finger or the like from touching it, the insecticide cartridge 2 is accommodated in the recipient recess 11 of the apparatus main body 1, and is covered with the cover 6. The cover 6 should be equipped with openings 61 so that it may not hinder the transpiration of the insecticide. It is desirable that the size of the openings 61 be as large as possible; when the strength of the cover 6 deteriorates as a result of the enlargement of the size of the openings 61, a reinforcing portion 62 is provided on the surface of the cover 6, whereby it is possible to enlarge the size of the openings 61 while securing the strength of the cover 6.

Further, it is desirable to provide an opening/closing switch 63 for opening and closing the cover when replacing the insecticide cartridge 2.

Materials of the apparatus main body 1, the insecticide cartridge 2, and the cover 6 are not specifically limited. However, from the viewpoint of productivity, moldability, price, weight, and the like, preferably, each of them may be prepared from a plastic resin, especially a polyester resin (e.g., polyethylene terephthalate having an intrinsic viscosity of 0.7 dl/g or less).

Figure 5:
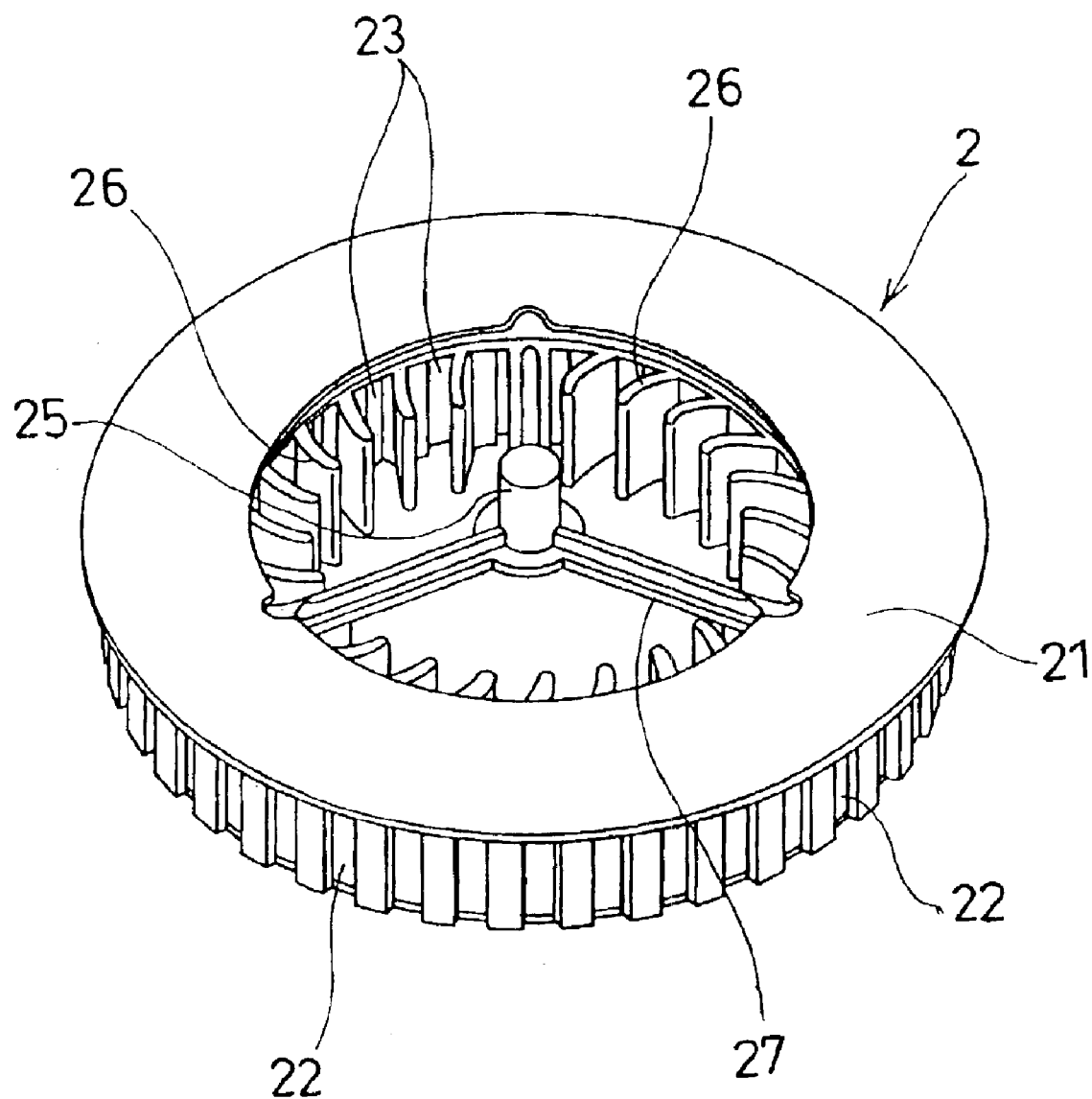
FIG. 5 is a perspective view as seen from above of an insecticide cartridge for use in the insecticide transpiration apparatus of the present invention.
Figure 6:
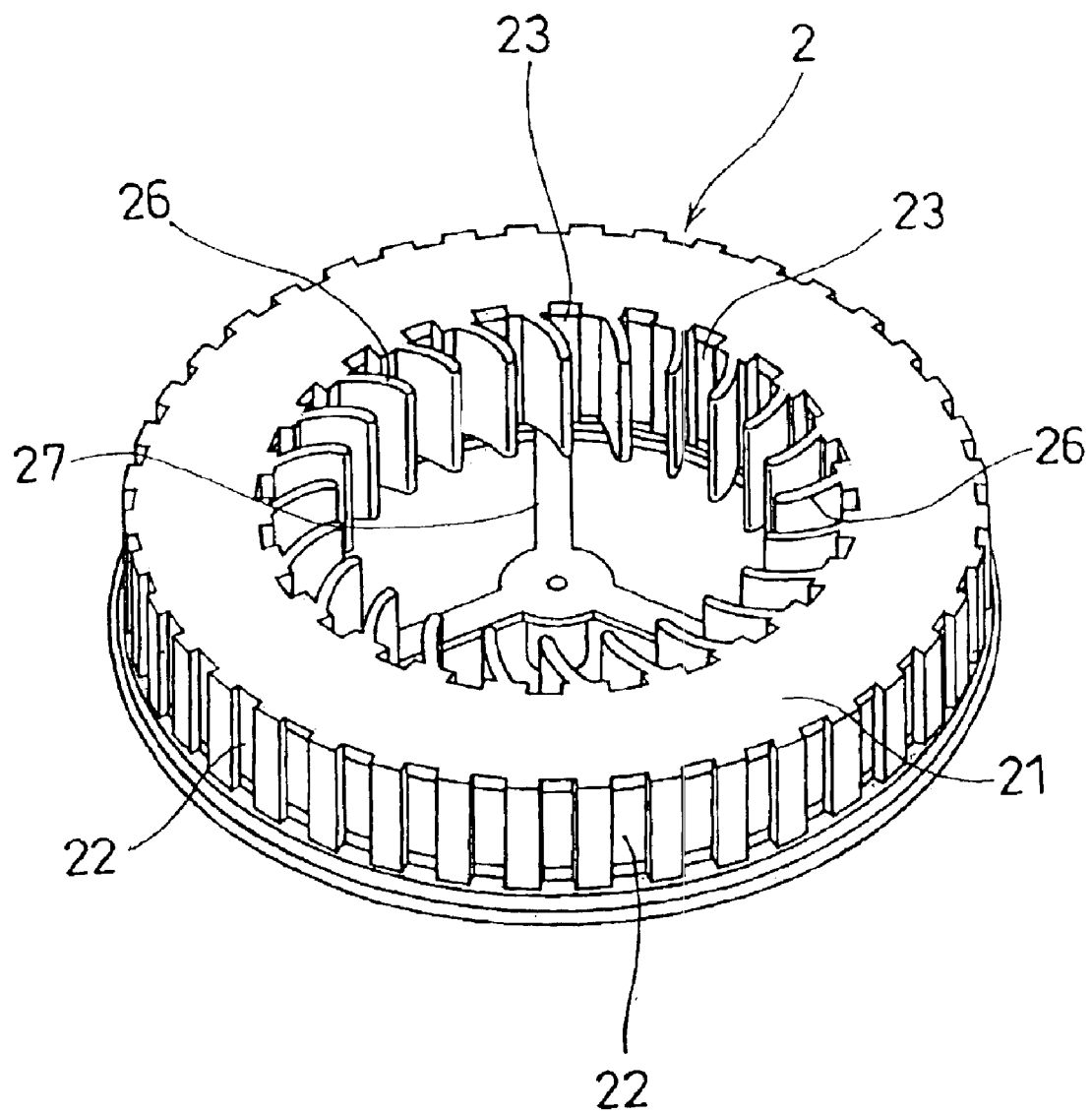
FIG. 6 is a perspective view as seen from below of an insecticide cartridge for use in the insecticide transpiration apparatus of the present invention.
Figure 7:
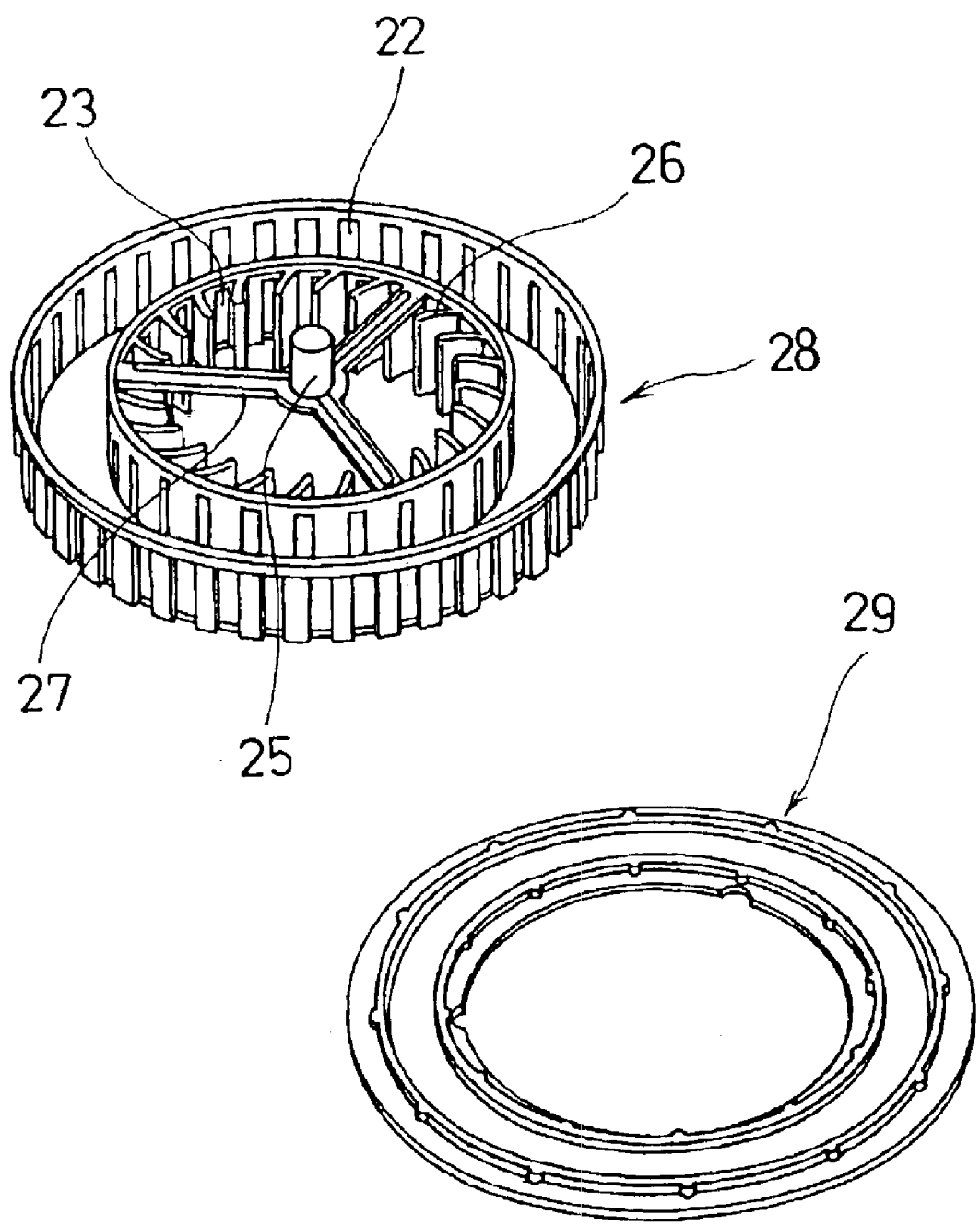
FIG. 7 is an exploded perspective view of an insecticide cartridge for use in the insecticide transpiration apparatus of the present invention.

The structure of the insecticide cartridge 2 will be described in more detail with reference to FIGS. 5 through 7.

The insecticide cartridge 2 consists of an annular hollow structure 21 with a rectangular sectional configuration; it is accommodated in the recipient recess 11 of the apparatus main body 1, and contains the insecticide-impregnated bodies 3. The size of the hollow structure 21 varies according to the amount of the insecticide-impregnated bodies 3 to be contained therein, the length of blade portions 26 to be provided, etc.

Further, in the outer peripheral surface and the inner peripheral surface of the insecticide cartridge 2, there are respectively provided outer peripheral surface openings 22 and inner peripheral surface openings 23. The outer peripheral surface openings 22 and the inner peripheral surface openings 23 consist of a large number of slits formed in parallel; they serve as the breathers through which the insecticide in the insecticide-impregnated bodies 3 transpires. The larger the size of the outer peripheral surface openings 22 and that of the inner peripheral surface openings 23, the higher the rate at which the insecticide transpires.

Further, on the inner peripheral surface of the insecticide cartridge 2, there are provided a large number of blade portions 26 extending toward the center of the annular insecticide cartridge 2. These blade portions 26 are formed integrally with the insecticide cartridge 2 so as not to block the inner peripheral surface openings 23; they are in the form of curved plates. When the insecticide cartridge 2 is rotated, the blade portions 24 promote passing of air from the inner peripheral surface toward the outer peripheral surface of the hollow structure 21. Thus, the blade portions 26 in the form of curved plates are capable of capturing more air and sending it with a stronger airflow.

The insecticide cartridge 2 of the present invention, in which the hollow structure 21 and the blade portions 26 are molded integrally, has been improved in the following points over the conventional insecticide cartridge in which the hollow structure and the blade portions are formed separately and then assembled:

1) In the insecticide cartridge in which the hollow structure and the blade portions are formed integrally, the blade portions can be made longer than in the insecticide cartridge in which they are formed separately and then assembled. As a result, it is possible to generate a stronger airflow.
2) In the insecticide cartridge in which the hollow structure and the blade portions are formed integrally, it is possible to diminish the distance between the insecticide-impregnated bodies and the blades of the blade portions. As a result, the airflow generated directly hits the insecticide-impregnated bodies before it weakens.
3) There is no need to separately produce the blade portions and the hollow structure and then assemble them.
4) It is possible to omit the operation of performing correct positioning on the blade portions and the hollow structure so that the blade portions may not block the openings provided in the inner peripheral surface of the hollow structure when mounting the blade portions on the hollow structure.

The above-mentioned features 1) and 2) constitute factors leading to an improvement in the efficiency with which the insecticide is transpired from the insecticide-impregnated bodies 3 contained in the insecticide cartridge 2; assuming that the conditions, such as the insecticide-impregnated bodies and the RPM of the insecticide cartridge, are the same, the insecticide cartridge 2 of the present invention, in which the blade portions 26 are formed integrally with the hollow structure 21, can transpire more insecticide than the conventional cartridge in which the blade portions and the hollow structure are formed separately. Conversely, by using the insecticide cartridge 2 of the present invention, it is possible to achieve a certain insecticide transpiration amount with less amount of insecticide-impregnated bodies or at less RPM of the insecticide cartridge, making it possible to lengthen the time of use of the insecticide transpiration apparatus.

The above-mentioned features 3) and 4) lead to a dramatic improvement in the productivity of the insecticide cartridge 2 of the present invention.

The insecticide cartridge 2 has the core portion 25 at the center of the annular hollow structure 21. In the example shown, the core portion 25 is a cylindrical member fitted onto the rotation support shaft 24 without play. The core portion 25 is connected to the hollow structure 21 by spoke portions 27.

When the insecticide cartridge 2 is composed of a main body member 28 forming an annular groove and a cover member 29 serving as the cover thereof, the production of the insecticide cartridge 2 and the accommodation of the insecticide-impregnated bodies 3 in the hollow structure 21 are facilitated. The engagement of the main body member 28 and the cover member 29 can be effected, for example, through fitting engagement by using ribs provided on the surface of the cover member 29; it is also possible to fix them together by using an adhesive or the like.

Figure 8:
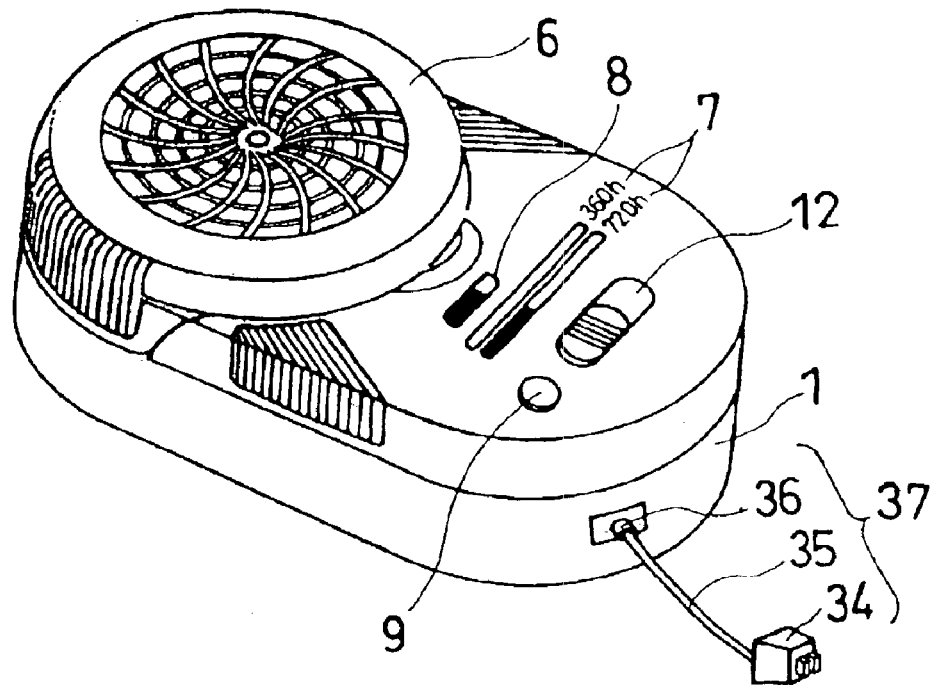
FIG. 8 is a perspective view of an insecticide transpiration apparatus according to the present invention equipped with an insecticide remaining amount indicating function and a battery remaining power indicating function.
Figure 9:
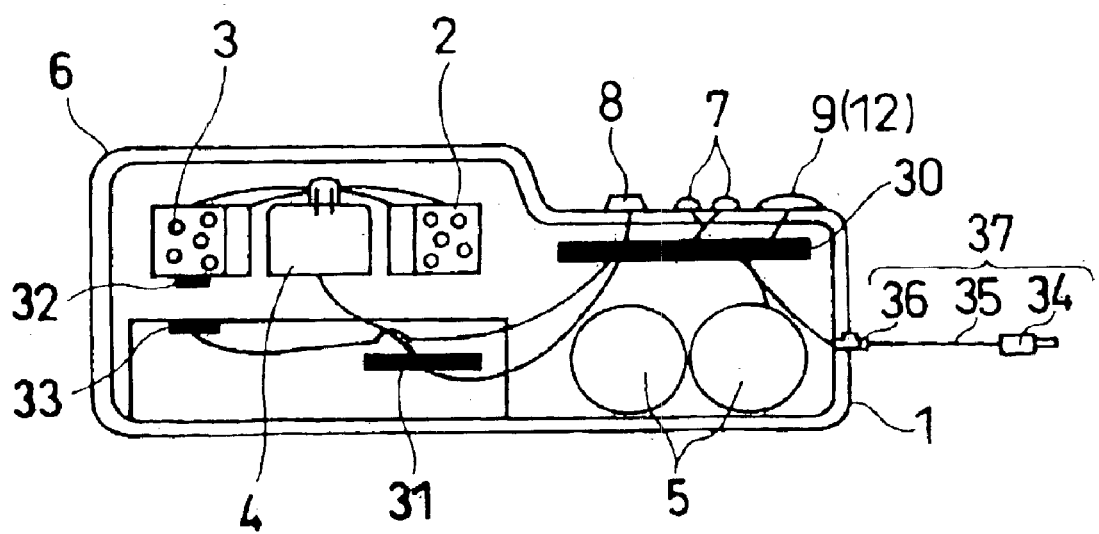
FIG. 9 is a sectional view of the insecticide transpiration apparatus shown in FIG. 8.
Figure 10:
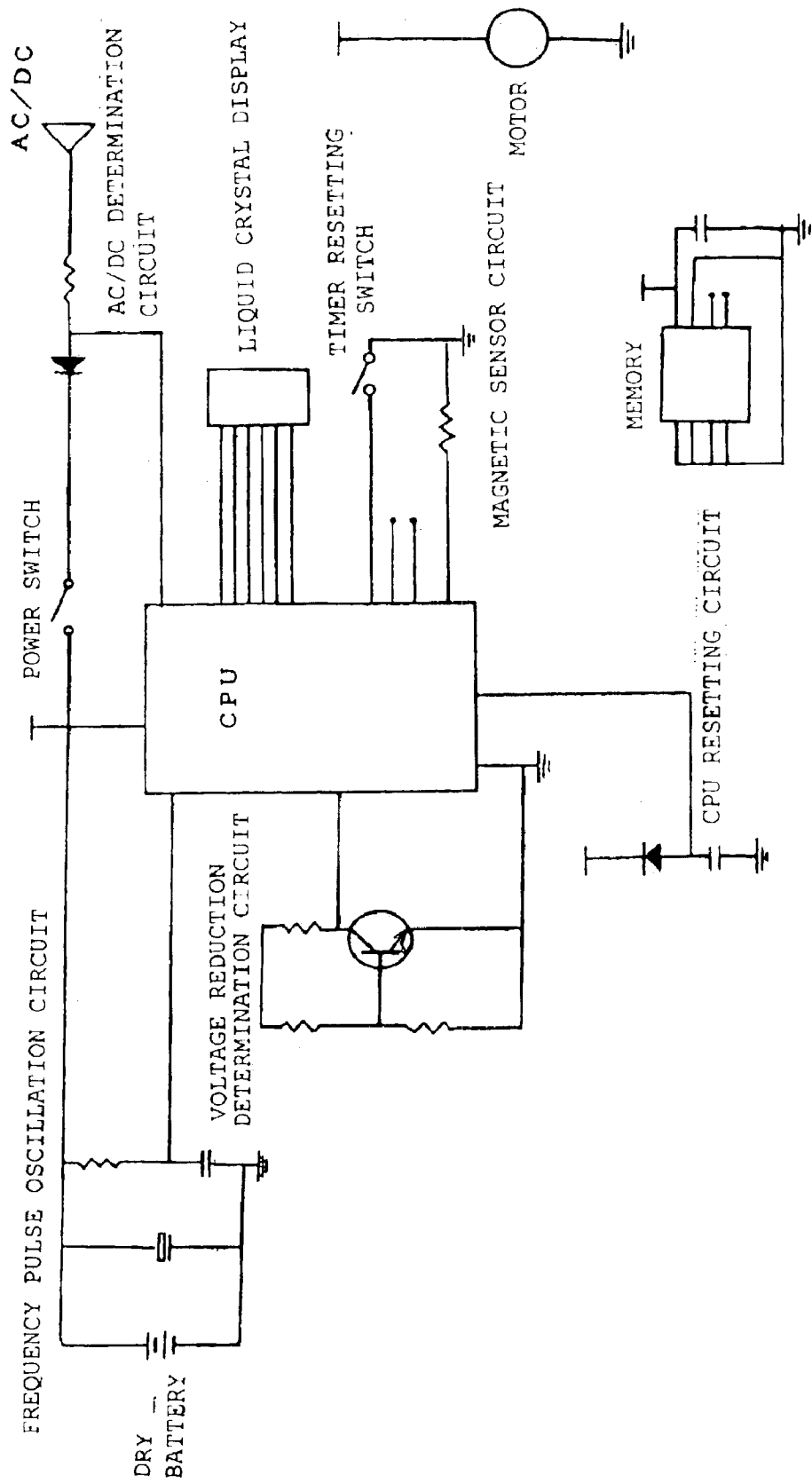
FIG. 10 is a diagram showing an electronic circuit for the insecticide transpiration apparatus shown in FIG. 8.

Next, an example of the insecticide transpiration apparatus equipped with an insecticide remaining amount indicating function and a battery remaining power indicating function will be described with reference to FIGS. 8 through 10. FIG. 8 is a perspective view of the apparatus, FIG. 9 is a sectional view thereof, and FIG. 10 is an electronic circuit diagram. The following description will be focused on the portions where this apparatus differs from the above-mentioned embodiments.

The apparatus uses as electric source both dry cells 5 and a direct current electric source 37 composed of an AC adapter 34, an AC cord 35 and a connector 36. In the vicinity of the power source switch 12 on the upper surface of the apparatus main body 1, there are arranged an insecticide remaining amount indicating liquid crystal display 7 and a battery remaining power indicating liquid crystal display 8, which are of a bar-like type that can be visually checked and, further, a reset switch 9. These are connected to a CPU power source circuit board 30 and a motor power source circuit board 31 for control. Further, a magnetic sensor 33 detects a magnetic tape 32 attached to the insecticide cartridge 2 to discern the type of the insecticide cartridge 2. In this example, it is possible to load the apparatus with insecticide cartridges 2 of different valid times of uses: 360 hours and 720 hours. The insecticide remaining amount indicating liquid crystal display 7 indicates the insecticide remaining amount of the insecticide cartridge 2, whose type is discerned, through liquid crystal. The battery remaining power indicating liquid crystal display 8 indicates the remaining power of the batteries through liquid crystal. When, after replacing the insecticide cartridge 2 with a new one, the reset switch 9 is depressed, the insecticide remaining amount measurement program is reset.

EXAMPLES

The present invention will now be described in more detail with reference to specific examples and test examples; these examples, however, are only given by way of illustration, and should not be construed restrictively.

Example 1

Preparation of Insecticide Transpiration Apparatus 1 with Insecticide Cartridge in which Hollow Structure and Blade Portions are Integrally Formed An annular hollow structure having an outer diameter of 62 mm, an inner diameter of 44 mm, and a height of 13 mm, and a rectangular sectional configuration was prepared. The hollow portion of the hollow structure had an outer diameter of 60 mm, an inner diameter of 42 mm, a height of 11 mm, and a volume of approximately 15.8 cm$^3$. In the outer peripheral surface of the hollow structure, 40 openings in the form of slits with a width of approximately 2 mm were provided at equal intervals. In the inner peripheral surface thereof, 24 openings in the form of slits with a width of approximately 2 mm were provided at equal intervals. Further, on the inner peripheral surface of the insecticide cartridge, 24 blade portions with a length of approximately 5 mm were integrally formed so as to be inclined at a fixed angle, thus completing the insecticide cartridge. The resultant distance as measured from the inner wall of the hallow structure to the forward end of each blade portion was 7 mm.

Further, a cylindrical core portion was provided at the center of the insecticide cartridge, and the core portion was connected to the hollow structure by three spoke portions.

The resulting insecticide cartridge is attached to a motor driven by two AA size batteries (3.0V in total) to give an insecticide transpiration apparatus. The test of insecticidal Effect described below was carried out with the apparatus.

Example 2

Preparation of Insecticide Transpiration Apparatus 2 with Insecticide Cartridge in which Hollow Structure and Blade Portions are Integrally Formed The same insecticide cartridge as Example 1 is attached to a motor driven by a DC electric source with 4.5V produced from an AC through an AC adapter and/or another DC electric source with two AA size batteries (3.0V in total).

Comparative Example 1

Preparation of Insecticide Transpiration Apparatus with Insecticide Cartridge in which Hollow Structure and Blade Portions are Formed Separately An annular hollow structure having the same dimensions and the same openings as those of Example 1 was prepared. Regarding the blade portions, a sirocco fan having an outer diameter approximately equal to the inner diameter of the hollow structure and equipped with a core portion and three spoke portions was separately prepared. The sirocco fan was inserted into the hollow structure to form an insecticide cartridge. The distance as measured from the inner wall of the hollow structure to the forward end of each blade portion was 7 mm, which is the same as that of the insecticide cartridge of Example 1. On the other hand, the length of the blade portions was 4.0 mm, which is less than that of the blade portions of the insecticide cartridge of Example 1 by 1.0 mm.

Test Example

An insecticide was impregnated in various kinds of raw materials for preparing insecticide impregnated materials. The resulting incident impregnated materials were housed in their respective insecticide cartridges of Example 1 and Comparative Example 1, followed by mounting each of them on an insecticide transpiration apparatus of the present invention. Subsequently, each of them was subjected to a measurement for estimating the transpiring amount of the chemical and a test for estimating insecticide effects on the first, fifteenth and thirtieth days while using the apparatus for twelve hours a day.

A test of insecticidal effect (knock-down effect) was performed by the open cylinder method according to the following procedures.

Procedures for Estimating the Insecticidal Effect of an Insecticidal Compound

Two plastic cylinders of 20 cm in inside diameter and 43 cm in height are piled up. A cylinder of 20 cm both in inside diameter and height is partitioned vertically with a wire net of 16 mesh (the place where the mosquitos are put in), and is placed thereon. A cylinder of 20 cm in inside diameter and height is further placed thereon. This set consisting of the four cylinders is placed on a stand, and an insecticide transpiration apparatus is placed in the middle of the stand to transpire the insecticidal ingredient in the chemical impregnated material to be examined. Then about 20 mosquitos to be tested are released in the upper stair of the cylinder set and the number of mosquitos knocked down is observed with the time elapsed.

Furthermore, the insecticidal effect was indicated as a relative effectiveness ratio in which an initial turning-over effect obtained by evaporation from a mosquito-repellent mat containing dl, d-cis, trans-allethrin (Pynamin Forte) on condition that a radiator plate of a heating unit is at a temperature of 160° C. The above test was repeated with various kinds of insecticides and the various amounts thereof, various chemical impregnated materials and various particle sizes thereof, various free-volumes of the insecticide cartridge, various rotational speeds of the motor, respectively.

The test results were listed in Tables 1 and 2, respectively.

In the tables, "Viscopearl" is the trade name of granular expandable cellulose beads manufactured by Rengo Co., Ltd., Japan. Furthermore, the compounds A to L used as the chemicals in the present test example denote the following, respectively:

Compound A: 2,3,5,6-tetrafluorobenzyl-chrysanthemate;
Compound B: 2,3,5,6-tetrafluorobenzyl-2,2-dimethyl-3-(1-propenyl)cyclopropane carboxylate;
Compound C: 4-methyl-2,3,5,6-tetrafluorobenzyl-chrysanthemate;
Compound D: 4-methyl-2,3,5,6-tetrafluorobenzyl-2,2-dimethyl-3-(1-propenyl)cyclopropane carboxylate;
Compound E: 4-methyl-2,3,5,6-tetrafluorobenzyl-2,2-dimethyl-3-(2,2-difluorovinyl)cyclopropane carboxylate;
Compound F: 4-methoxymethyl-2,3,5,6-tetrafluorobenzyl-chrysanthemate;
Compound G: 4-methoxymethyl-2,3,5,6-tetrafluorobenzyl-2,2-dimethyl-3-(1-propenyl)cyclopropane carboxylate;
Compound H: 2,3,4,5,6-pentafluorobenzyl-2,2-dimethyl-3-(2-chloro-2-trifluoromethylvinyl)cyclopropane carboxylate;
Compound I; 4-propargyl-2,3,5,6-tetrafluorobenzyl-3-(1-propenyl)-2,2-dimethylcyclopropane carboxylate;
Compound J: 4-methoxymethyl-2,3,5,6-tetrafluorobenzyl-2,2,3,3-tetramethylcyclopropane carboxylate; and
Compound K: 4-propargyl-2,3,5,6-tetrafluorobenzyl-2,2,3,3-tetramethylcyclopropane carboxylate.

TABLE 1

Test results obtained using the chemical transpiration apparatus with the insecticide cartridge prepared in Example 1

|   | Chemical (mg) | Particle size (mm) of chemical impregnated material | Free volume (%) | Rotational speed of motor (rpm) | Transpiring amount (mg/12 hours) 1 d | 15 d | 30 d | Insecticidal effect 1 d | 15 d | 30 d |
|---|---|---|---|---|---|---|---|---|---|---|
| 1 | Compound A | Viscopearl 3 | 40 | 1800 | 7.1 | 7.1 | 6.9 | 3.9 | 3.8 | 3.8 |
| 2 | Compound B | Pulp 4 | 20 | 2000 | 5.8 | 5.7 | 5.7 | 2.8 | 2.7 | 2.7 |
| 3 | Compound C | Ethylene-vinyl acetate 7 | 50 | 1300 | 2.7 | 2.6 | 2.5 | 2.3 | 2.2 | 2.2 |
| 4 | Compound D | Paper 6 | 65 | 1100 | 3.9 | 3.8 | 3.7 | 3.2 | 3.2 | 3.1 |
| 5 | Compound E | Polypropylene 5 | 25 | 1400 | 3.7 | 3.7 | 3.6 | 2.9 | 2.8 | 2.8 |
| 6 | Compound F | Pulp 8 | 70 | 200 | 1.2 | 1.0 | 1.0 | 2.6 | 2.5 | 2.5 |

TABLE 1-continued

Test results obtained using the chemical transpiration apparatus with the insecticide cartridge prepared in Example 1

| | Chemical (mg) | Particle size (mm) of chemical impregnated material | Free volume (%) | Rotational speed of motor (rpm) | Transpiring amount (mg/12 hours) | | | Insecticidal effect | | |
|---|---|---|---|---|---|---|---|---|---|---|
| | | | | | 1 d | 15 d | 30 d | 1 d | 15 d | 30 d |
| 7 | Compound G | Viscopearl 3 | 35 | 1200 | 2.1 | 2.0 | 2.0 | 3.4 | 3.4 | 3.4 |
| 8 | Compound H | Paper 5 | 40 | 500 | 1.3 | 1.3 | 1.2 | 2.4 | 2.3 | 2.3 |
| 9 | Compound I | Viscopearl 4 | 30 | 1100 | 3.3 | 3.2 | 3.2 | 3.0 | 2.9 | 2.9 |
| 10 | Compound J | Viscopearl 3 | 30 | 1200 | 4.5 | 4.4 | 4.4 | 2.9 | 2.8 | 2.8 |
| 11 | Compound K | Viscopearl 4 | 30 | 1300 | 4.4 | 4.3 | 4.2 | 2.8 | 2.7 | 2.7 |

TABLE 2

Test results obtained using the chemical transpiration apparatus with the insecticide cartridge prepared in Comparative Example 1

| | Chemical (mg) | Particle size (mm) of chemical impregnated material | Free volume (%) | Rotational speed of motor (rpm) | Transpiring amount (mg/12 hours) | | | Insecticidal effect | | |
|---|---|---|---|---|---|---|---|---|---|---|
| | | | | | 31 d | 15 d | 30 d | 1 d | 15 d | 30 d |
| 1 | Compound A | Viscopearl 3 | 40 | 1800 | 6.3 | 6.2 | 6.2 | 3.4 | 3.3 | 3.3 |
| 2 | Compound B | Pulp 4 | 20 | 2000 | 5.3 | 5.1 | 5.1 | 2.2 | 2.1 | 2.0 |
| 3 | Compound C | Ethylene-Vinyl acetate 7 | 50 | 1300 | 2.1 | 1.9 | 1.9 | 1.8 | 1.7 | 1.6 |
| 4 | Compound D | Paper 6 | 65 | 1100 | 3.3 | 3.2 | 3.1 | 2.8 | 2.7 | 2.6 |
| 5 | Compound E | Polypropylene 5 | 25 | 1400 | 3.2 | 3.1 | 3.1 | 2.4 | 2.3 | 2.3 |
| 6 | Compound F | Pulp 8 | 70 | 200 | 0.6 | 0.5 | 0.3 | 1.9 | 1.7 | 1.5 |
| 7 | Compound G | Viscopearl 3 | 35 | 1200 | 1.5 | 1.4 | 1.3 | 2.9 | 2.8 | 2.9 |
| 8 | Compound H | Paper 5 | 40 | 500 | 0.7 | 0.6 | 0.6 | 1.9 | 1.7 | 1.7 |
| 9 | Compound I | Viscopearl 4 | 30 | 1100 | 2.9 | 2.7 | 2.6 | 2.6 | 2.5 | 2.4 |
| 10 | Compound J | Viscopearl 3 | 30 | 1200 | 4.0 | 3.8 | 3.7 | 2.5 | 2.4 | 2.4 |
| 11 | Compound K | Viscopearl 4 | 30 | 1300 | 4.0 | 3.8 | 3.7 | 2.3 | 2.2 | 2.1 |

According to the insecticide transpiration apparatus of the present invention, as shown in Table 1, it was observed that the transpiring amount of the chemical had been stable for a long period of 30 days while a high insecticidal effect of the chemical had been kept during such a period. In other words, it was found that an excellent chronological stability of the chemical could be attained using the insecticide transpiration apparatus with the insecticide cartridge of the type of Example 1 since the transpiring amount of the chemical was almost constant without substantial variation with time and the insecticidal effect thereof was substantially constant for 30 days.

In the case of the insecticide cartridge of the Comparative Example 1 prepared by separately molding a hollow structural body for housing the chemical impregnated material therein and a wing portion, the transpiring effect thereof compares substantially unfavorably with that of the insecticide transpiration apparatus using the insecticide cartridge of the Example 1 as shown in Table 2.

The insecticide transpiration apparatus of the present invention follows procedures for accelerating the transpiration of chemicals from the chemical impregnated material by a current of air, without heating. Therefore, there is no need to worry about getting burnt through usage. In addition, an almost constant amount of the chemical can be stably transpired for a long time, so that for the first time ever an excellent insecticidal effect can be kept for a long period of time more than ever. Besides, the insecticide transpiration apparatus of the present invention is also excellent in safety, usability, and so on, compared with the conventional one. Therefore, it serves as a very useful function in pest control of insanitary insects such as mosquitoes and flies; offensive insects such as simulium flies, chironomids, *Tinea*. sp, *Tineola*. sp, and *Dermestidae*. Sp; but especially in pest control of mosquitoes.

The insecticide transpiration apparatus of the present invention can be constructed to be compact and lightweight so as to be actuated by a battery. Therefore, it can be useful not only for indoor but also for outdoor. Thus, for example, it has a very useful function in pest control of insanitary insects and of offensive insects in a room where the user is staying while on a journey or in a camping tent.

In the insecticide cartridge to be used in the insecticide transpiration apparatus of the present invention, a hollow structural body for housing the chemical impregnated material therein and a wing portion are integrally molded together. Therefore, it is possible to generate a current of air much stronger than that of the conventional one which directly blows on the chemical impregnated material without weakening the current of air. These facts contribute to the improvement in transpiring efficiency. Furthermore, it is possible to avoid the need of individually preparing the wing portion and the hollow structural body and combining them together. In addition, it is also possible to avoid the troublesome determination of positioning the hollow structural body and the wing portion, so that it can also be advantageous for productivity.

In the present invention, furthermore, the insecticide cartridge may be formed from a polyester resin, especially from polyethylene terephthalate (more preferably one having an intrinsic viscosity of 0.7 dl/g or less). In this case, therefore, the sustained release of chemical ingredients can be effectively performed without loss during the long-term usage. In addition, there is no substantial loss of the chemical during the long-term storage, so that it can be very advantageous.

Further, due to the provision of the insecticide remaining amount indicating function and the battery remaining power indicating function, it is possible to ascertain correctly and clearly the remaining service life of the insecticide cartridge and of the batteries and the remaining amount of the insecticide, which is useful and of practical value.

What is claimed is:

1. An insecticide transpiration apparatus including:
   an apparatus main body having a recipient capable of accommodating an insecticide cartridge;
   an insecticide cartridge rotatably supported in the recipient;
   a driving means which is composed of a motor connected to a rotation support shaft of the insecticide cartridge and an electric source and which is contained in the apparatus main body; and
   a cover pivoted to the apparatus main body so as to cover the insecticide cartridge in the recipient,
   wherein the insecticide cartridge includes:
      an annular hollow structure which has openings in an inner peripheral surface and an outer peripheral surface thereof;
      a core portion situated at the center of the annular hollow structure and connected to the rotation support shaft;
      a plurality of spoke portions connecting the core portion and the annular hollow structure; and
      blade portions integrally formed with the annular hollow structure so as to extend from the inner peripheral surface toward the center thereof and adapted to promote passing of air from the inner peripheral surface to the outer peripheral surface of the annular hollow structure;
   wherein:
      granular insecticide-impregnated bodies are accommodated within the annular hollow structure; and
      the blade portions are arcuate or curved blades having a length of at least 5 mm or more.

2. An insecticide transpiration apparatus according to claim 1, wherein the annular hollow structure is composed of a main body member and a cover member engaged therewith.

3. An insecticide transpiration apparatus according to claim 1, wherein the openings consist of a multitude of opening slits formed in parallel.

4. An insecticide transpiration apparatus including:
   an apparatus main body having a recipient capable of accommodating an insecticide cartridge;
   an insecticide cartridge rotatably supported in the recipient;
   a driving means which is composed of a motor connected to a rotation support shaft of the insecticide cartridge and an electric source and which is contained in the apparatus main body; and
   a cover pivoted to the apparatus main body so as to cover the insecticide cartridge in the recipient,
   wherein the insecticide cartridge includes:
      an annular hollow structure which has openings in an inner peripheral surface and an outer peripheral surface thereof;
      a core portion situated at the center of the annular hollow structure and connected to the rotation support shaft;
      a plurality of spoke portions connecting the core portion and the annular hollow structure; and
      blade portions, consisting of arcuate or curved blades having a length of at least 5 mm or more, integrally formed with the annular hollow structure so as to extend from the inner peripheral surface toward the center thereof and adapted to promote passing of air from the inner peripheral surface to the outer peripheral surface of the annular hollow structure; and
   wherein granular insecticide-impregnated bodies are accommodated within the annular hollow structure at a void ratio of 20 to 70%, and wherein the granular insecticide-impregnated bodies include a substrate made of paper, pulp, cellulose-based carrier or synthetic resin carrier, or a mixture thereof, and the granular insecticide-impregnated bodies have an average outer diameter of 3 to 10 mm and a size not less than 1.3 times that of the openings;
   wherein the insecticide-impregnated bodies include one or more fluorine-substituted benzyl alcohol ester compound represented by formula (I):

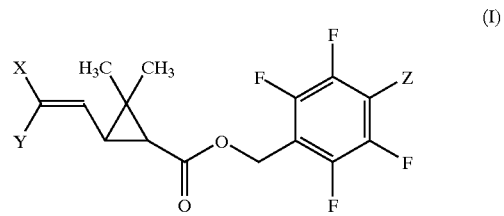

wherein X and Y are identically or differently represent hydrogen atom, methyl group, halogen atom or trifluoromethyl group, and Z represents hydrogen atom, fluorine atom, methyl group, methoxymethyl group or propargyl group; and
   wherein the fluorine-substituted benzyl alcohol ester compound can be transpired from the insecticide-impregnated bodies at a transpiring amount of 0.01 to 0.6 mg per hour for 180 hours or more.

5. An insecticide transpiration apparatus including:
   an apparatus main body having a recipient capable of accommodating an insecticide cartridge;
   an insecticide cartridge rotatably supported in the recipient;

a driving means which is composed of a motor connected to a rotation support shaft of the insecticide cartridge and an electric source and which is contained in the apparatus main body; and a cover pivoted to the apparatus main body so as to cover the insecticide cartridge in the recipient, wherein the insecticide cartridge includes:

an annular hollow structure which has openings in an inner peripheral surface and an outer peripheral surface thereof;

a core portion situated at the center of the annular hollow structure and connected to the rotation support shaft;

a plurality of spoke portions connecting the core portion and the annular hollow structure; and blade portions integrally formed with the annular hollow structure so as to extend from the inner peripheral surface toward the center thereof and adapted to promote passing of air from the inner peripheral surface to the outer peripheral surface of the annular hollow structure;

wherein:

granular insecticide-impregnated bodies are accommodated within the annular hollow structure; and the insecticide-impregnated bodies have an average outer diameter of 3 to 10 mm and a size not less than 1.3 times that of the openings.

6. An insecticide transpiration apparatus including:

an apparatus main body having a recipient capable of accommodating an insecticide cartridge;

an insecticide cartridge rotatably supported in the recipient;

a driving means which is composed of a motor connected to a rotation support shaft of the insecticide cartridge and an electric source and which is contained in the apparatus main body; and a cover pivoted to the apparatus main body so as to cover the insecticide cartridge in the recipient, wherein the insecticide cartridge includes:

an annular hollow structure which has openings in an inner peripheral surface and an outer peripheral surface thereof;

a core portion situated at the center of the annular hollow structure and connected to the rotation support shaft;

a plurality of spoke portions connecting the core portion and the annular hollow structure; and blade portions integrally formed with the annular hollow structure so as to extend from the inner peripheral surface toward the center thereof and adapted to promote passing of air from the inner peripheral surface to the outer peripheral surface of the annular hollow structure;

wherein:

granular insecticide-impregnated bodies are accommodated within the annular hollow structure; and the insecticide-impregnated bodies are accommodated in the insecticide cartridge at a void ratio of 20 to 70%.

7. An insecticide transpiration apparatus according to claim 1, wherein the insecticide-impregnated bodies include one or more fluorine-substituted benzyl alcohol ester compound represented by formula (I):

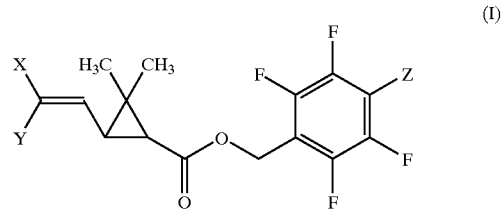

wherein X and Y are identically or differently represent hydrogen atom, methyl group, halogen atom or trifluoromethyl group, and Z represents hydrogen atom, fluorine atom, methyl group, methoxymethyl group or propargyl group.

8. An insecticide transpiration apparatus according to claim 1, wherein the insecticide-impregnated bodies include a chemical selected from 2,3,5,6-tetrafluorobenzyl-chrysanthemate, 2,3,5,6-tetrafluorobenzyl-2,2-dimethyl-3-(1-propenyl)cyclopropane carboxylate, 4-methyl-2,3,5,6-tetrafluorobenzyl-chrysanthemate, 4-methyl-2,3 ,5,6-tetrafluorobenzyl-2,2-dimethyl-3-(2,2-dichlorovinyl) cyclopropane carboxylate, 4-methyl-2,3,5,6-tetrafluorobenzyl-2,2dimethyl-3-(2,2-difluorovinyl) cyclopropane carboxylate, 4-methoxymethyl-2,3,5,6-tetrafluorobenzyl-chrysanthemate, 4-methoxymethyl-2,3,5, 6-tetrafluorobenzyl-2,2, dimethyl-3-(1-propenyl) cyclopropane carboxylate, 2,3,4,5,6-pentafluorobenzyl-2,2-dimethyl-3-(2-chloro-2-trifluoromethylvinyl)cyclopropane carboxylate, 4-propargyl-2,3 ,5,6-tetrafluorobenzyl-3-(1-propenyl)-2,2-dimethylcyclopropane carboxylate, 4-methoxymethyl-2,3,5,6-tetrafluorobenzyl-2,2,3, 34tetramethylcyclopropane carboxylate and 4-propargyl-2,3,5,6-tetrafluorobenzyl-2,2,3,3-tetramethylcyclopropane carboxylate, or mixtures thereof.

9. An insecticide transpiration apparatus according to claim 1, wherein the insecticide-impregnated bodies include 60 mg or more of a chemical.

10. An insecticide transpiration apparatus according to claim 1, wherein the insecticide-impregnated bodies include a substrate made of paper, pulp, cellulose-based carrier or synthetic resin carrier, or a mixture thereof.

11. An insecticide transpiration apparatus according to claim 1, wherein the rotational frequency of the motor is in the range of 500 to 2000 rpm.

12. An insecticide transpiration apparatus according to claim 1, wherein the chemical can be transpired from the insecticide-impregnated bodies at a transpiring amount of 0.01 to 0.6 mg per hour for 180 hours or more.

13. An insecticide transpiration apparatus according to claim 1, wherein the insecticide cartridge is made of a polyester resin.

14. An insecticide transpiration apparatus according to claim 13, wherein the polyester resin is polyethylene terephthalate.

15. An insecticide transpiration apparatus according to claim 14, wherein the polyethylene terephthalate has an intrinsic viscosity of 0.7 dl/g or less.

16. An insecticide transpiration apparatus according to claim 1, further including an insecticide remaining amount display function realized by liquid crystal and allowing visual inspection.

17. An insecticide transpiration apparatus according to claim 16, wherein the insecticide remaining amount display function is in correspondence with a plurality of insecticide cartridges of different valid periods of use, wherein a magnetic sensor or an optical sensor adapted to detect a signal from a magnetic tape or a metal member attached to the cartridge is provided on the surface of the insecticide transpiration apparatus opposed to the cartridge, and wherein a central processing unit receives the signal detected by the sensor to recognize the kind of cartridge.

18. An insecticide transpiration apparatus according to claim 16, which contains a circuit adapted to emit pulses of a natural frequency with the operation of the motor, wherein the central processing unit detects these pulses emitted to measure the motor operation time on the basis thereof and controls the display of the insecticide remaining amount.

19. An insecticide transpiration apparatus according to claim 1 or 16, further including a battery remaining power indicating function realized by liquid crystal and allowing visual inspection.

20. An insecticide transpiration apparatus according to claim 19, wherein the battery remaining power indicating function is realized by a display portion, a voltage reduction detecting circuit, and a central processing unit adapted to recognize a reduction in battery voltage and control the battery remaining power indication on the basis of the recognition.

* * * * *